(12) United States Patent
Scholz et al.

(10) Patent No.: US 10,736,938 B2
(45) Date of Patent: *Aug. 11, 2020

(54) METHOD FOR THE TREATMENT OF ACNE

(71) Applicant: Active Micro Technologies, LLC, Lincolnton, NC (US)

(72) Inventors: Durant Scholz, Lincolnton, NC (US); Erica Segura, Denver, NC (US)

(73) Assignee: Active Micro Technologies, LLC, Lincolnton, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/205,883

(22) Filed: Nov. 30, 2018

(65) Prior Publication Data

US 2019/0099469 A1 Apr. 4, 2019

Related U.S. Application Data

(63) Continuation of application No. 15/424,037, filed on Feb. 3, 2017, now Pat. No. 10,159,708.

(60) Provisional application No. 62/291,587, filed on Feb. 5, 2016.

(51) Int. Cl.
| | | |
|---|---|---|
| *A61K 38/00* | (2006.01) | |
| *A61K 9/00* | (2006.01) | |
| *C07K 14/47* | (2006.01) | |
| *A61P 17/10* | (2006.01) | |
| *A61P 17/00* | (2006.01) | |
| *A61K 38/16* | (2006.01) | |
| *A61K 35/744* | (2015.01) | |

(52) U.S. Cl.
CPC .......... *A61K 38/164* (2013.01); *A61K 9/0014* (2013.01); *A61K 35/744* (2013.01); *A61K 38/00* (2013.01)

(58) Field of Classification Search
CPC .... A61K 35/744; A61K 38/00; A61K 38/164; A61K 9/0014; A61K 9/00; C07K 14/195; C07K 14/4723; C07K 14/47; A61P 17/10; A61P 17/00
USPC ........................................... 514/2.3; 530/300
See application file for complete search history.

(56) References Cited

U.S. PATENT DOCUMENTS

2010/0129305 A1 * 5/2010 Lee .......................... A61K 8/31 424/63
2011/0020302 A1   1/2011 Banov et al.

OTHER PUBLICATIONS

Barney, Alicia, "How to Choose Your Best Acne Treatment" from www.webmd.com, pp. 1-5. Accessed Jul. 1, 2019.*
"What Are the End Products of Fermentation?" from www.reference.com/science/end-products-fermentation, pp. 1-4. Accessed Jul. 1, 2019.*
A0A1B2A1L8 from UniProt, pp. 1-10, Integrated into UniProtKB/TrEMBL on Nov. 2, 2016. (Year: 2016).*
Spotlight On: Leucidal—FutureDerm from https://www/futurederm.com/spotlight-on-leucidal/, pp. 1-7, Sep. 15, 2014. (Year: 2014).*
Everyday Compounds—Salicylic Acid from https://compoundchem.com/2014/03/17/everyday-compounds-salicylic-acid/, pp. 2-6, Mar. 17, 2014. (Year: 2014).*
Li et al, "Idnetification of Didecyldimethylammonium Salts and Salicylic Acid as Antimicrobial Compounds in Commercial Fermented Radish Kinnchi," Journal of Agricultural and Food Chemistry, 2015, 63: 3053-3058. (Year: 2015).*

* cited by examiner

*Primary Examiner* — Julie Ha
(74) *Attorney, Agent, or Firm* — Lerner, David, Littenberg, Krumholz & Mentlik, LLP

(57) ABSTRACT

Compositions and methods for the treatment of acne are disclosed herein. In one embodiment, a method for the treatment of acne includes applying a composition to the affected area, wherein the composition comprises a fermentation product derived from *Leuconostoc* bacterium.

5 Claims, No Drawings

METHOD FOR THE TREATMENT OF ACNE

CROSS-REFERENCE TO RELATED APPLICATIONS

This application is a continuation of U.S. application Ser. No. 15/424,037, filed Feb. 3, 2017, which claims the benefit of U.S. Application No. 62/291,587, filed Feb. 5, 2016, the disclosures of which are incorporated herein by reference.

BACKGROUND OF THE INVENTION

The present invention relates to the treatment of acne and more particularly to the use of an antimicrobial peptide derived from fermentation as an effective ingredient in acne treatments.

Acne is characterized by whiteheads, blackheads, pimples, and greasy skin. Acne can be very embarrassing and can lead to anxiety and low self-esteem among those who have it. In addition to possible physical consequences such as scarring, the mental effects of acne push many to try a variety of treatments. Conventional treatment options to improve the appearance of acne include lifestyle changes, and medications. Some medications include side effects such as itching and burning skin.

Excessive growth of bacteria is often part of acne. It is believed that the bacteria normally present on the skin *Propionibacterium acnes* is usually the bacteria involved. Among many treatments for acne, it is believed that traditional preservatives such as, Phenoxy Ethanol, and Parabens, are not effective against acne. Conventional treatments for acne often include salicylic acid. Salicylic acid works only as a free acid. Salicylates are salts or esters of salicylic acid and it is believed that they do not work as a treatment for acne. Therefore, there is a need for a product that does not cause the side effects that salicylic acid causes in the treatment of acne.

BRIEF DESCRIPTION OF THE INVENTION

The technology described herein a method for the use of an antimicrobial peptide derived from fermentation for the treatment of acne.

According to one aspect of the technology described herein, there is provided a method for the treatment of acne using a composition that includes fermentation products.

DETAILED DESCRIPTION OF THE INVENTION

The present invention provides a method for the use of a treatment for acne that includes fermentation products of *leuconostoc* bacterium. These fermentation products include an antimicrobial peptide derived from fermentation. This is unexpected because antimicrobial peptides derived from fermentation are not conventional agents used for the treatment of acne. This is because antimicrobial peptides derived from fermentation contain natural salicylates. Salicylates are not a conventional treatment for acne even though they can be derived from salicylic acid. Salicylic acid is a common ingredient in anti-acne reparations, but is generally only effective at very low pHs. Such low pHs allow the acid to remain in its free form.

Antimicrobial peptides derived from fermentation available commercially as Leucidal® available from Active Micro Technologies (AMT). Thus according to the present invention, Leucidal® liquid is provided for use as an ingredient for acne treatments.

Salicylic acid is not present in antimicrobial peptides derived from fermentation in its free form because the pH of antimicrobial peptides derived from fermentation is too high. In this regard, the pH of antimicrobial peptides derived from fermentation ranges from about 3.0 to about 5.0. Further confirmation that salicylic acid is not the active agent in antimicrobial peptides derived from fermentation is that if salicylic acid acne preparations were increased to such a pH, the salicylic acid would no longer remain in its free form. Thus the activity of the product would plummet.

The fermentation products of the *leuconostoc* bacterium of the present invention include salicylates. The salicylates are salts and esters of salicylic acid in the fermentation products used in the present invention include a mixture of salicylate forms, not one single salicylic. By way of example and not limitation salicylate forms included in the fermentation products of *Leuconostoc* bacterium of the present invention can include one of the following: sodium salicylate, $C_7H_5NaO_3$; methyl salicylate, $C_8H_8NaO_3$; and a combination thereof.

The efficacy of antimicrobial peptides derived from fermentation when used in preparations for acne treatment has been shown in studies.

*Propionibacterium acnes* is a gram positive, non-spore-forming, microaerophilic, rod-shaped bacterium that is a common inhabitant of human skin. This microorganism metabolizes fatty acids created by sebaceous glands. The combination of fatty acid metabolites and antigens produced by the bacteria can create intense localized areas of inflammation that can fracture hair follicles. As a consequence, lesions develop on the surface of the skin in the form of pustules. This condition is commonly known as acne.

The purpose of this study was to determine the bactericidal efficacy of antimicrobial peptides derived from fermentation against *P. acnes* by establishing the minimum inhibitory concentration (MIC) required to inhibit its growth and proliferation. For comparative purposes, an over-the-counter acne treatment product was used as a benchmark. According to the results, antimicrobial peptides derived from fermentation is capable of effectively inhibiting the growth of *P. acnes* at a significantly lower concentration than that of the benchmark product.

The compounds of the present invention, i.e., antimicrobial peptides derived from fermentation, were tested for efficacy. An over-the-counter, deep cleaning astringent that contains 2% salicylic acid was also tested as a benchmark. For comparison. Each product was tested by preparing a serial dilution in a growth medium, beginning with an initial product concentration of 100%. The antimicrobial peptides derived from fermentation were those that can be obtained commercially as Leucidal.

To determine the Minimum Inhibitory Concentration (MIC) of each product against *P. acnes*, a standard 9% saline solution was added to a test tube using a sterile pipettor. Enough bacteria were added to the saline solution using a sterile loop to match the turbidity of a 0.5 McFarland standard. Two milliliters of this bacterial suspension were then transferred to one additional milliliter of 9% saline solution. Afterwards, 300 µL of the diluted mixture were added to 30 ml of sterile water yielding a final bacterial concentration of approximately 106 colony forming units (cfu)/ml. using an 8-tip pipettor, 150 µL of double strength Tryptic Soy Broth (TSB) were added to the first row of wells in a sterile microwell plate. Then, 150 μL of single strength TSB were pipetted into the remaining rows of the plate.

150 μL of antimicrobial peptides derived from fermentation was pipetted into the first row of wells containing the double-strength TSB and mixed 5 times. 150 μL of this mixed material from the first row were then transferred via pipettor into the second row of wells and mixed 5 times. This procedure was repeated for each subsequent row, creating a serial dilution of the antimicrobial peptides derived from fermentation ranging from 50% to 0.05% concentration through the first 11 rows of the plate. The last row did not receive any of the serially diluted antimicrobial peptides derived from fermentation. This twelfth row, containing only single strength TSB, served as a positive control to demonstrate the viability of the diluted bacterial culture used to inoculate the plate. This same procedure was then repeated using the over-the-counter benchmark product.

Each plate was inoculated using an inoculating plate that had been dipped in the *P. acnes* inoculum suspension, prepared as previously described. The plates were incubated for 48 hours at 35+/−2° C. After the 48-hour incubation period the plates were examined for microbial growth, indicated by turbidity in the wells. The row of wells with the lowest concentration of tested product that remained clear (i.e., inhibited growth) was used to establish the MIC value. The MIC of the compounds of the present invention was 1.6. The MIC of the benchmark product was 12.5.

Based on these results, it can be concluded that antimicrobial peptides derived from fermentation is capable of inhibiting the growth of *Propionibacterium acnes* when used at a concentration of approximately 1.5%. This concentration is significantly lower than the 12.5% concentration that is required to equally inhibit growth when using the benchmark product containing 2% salicylic acid.

*P. acnes* has been identified as the primary factor that causes acne. By inhibiting the proliferation of this bacterium, one may significantly minimize acne formation. Antimicrobial peptides derived from fermentation are a broad-spectrum antimicrobial that has been shown to be effective against the acne-causing bacterium *Propionibacterium acnes*. These properties make antimicrobial peptides derived from fermentation an effective ingredient for formulations developed to address problem skin.

The present invention can be better understood by a description of the use of thereof. There is provided herein a method for treating acne using antimicrobial peptides. More specifically there is a method provided for treating acne using antimicrobial peptides derived from fermentation. The antimicrobial peptides are provided in Leucidal® liquid. A specific treatment composition for topical use includes water, Leucidal® liquid, an oil in water emulsifier (available under the brand name Liposorb L-20) and xanthan gum (available under the brand name Keltrol) in the following proportions by weight: Water about 84%, Leucidal® liquid about 10%, Liposorb L-20 about 5%, and Keltrol about 1%. More generally, the following proportions are preferable: Water between about 75% and about 95%, Leucidal® liquid between about 5% and about 20%, Liposorb L-20 between about 2.5% and about 10%, and Keltrol between about 0.5% and about 2%.

The treatment composition is applied topically to the acne affected facial areas. The treatment composition can be applied twice per day. For example, the treatment can be applied in morning and in evening. The treatment composition can be applied with a cotton swab.

A treatment composition as described above was used in an investigation into the efficacy of the composition over 42 days. The results of the investigation indicated that the treatment composition was effective at reducing facial acne. The mean number of total acne lesions was reduced by 41.82%. In addition the overall appearance of the skin was improved. According to data obtained via Photogrammetrix™ Image Analysis, the treatment composition educed facial acne by an average of 68.65% over a 42 day period. The maximum improvement over the 42 day period was 93.0%.

The foregoing has described treatment for acne using antimicrobial peptides derived from fermentation and all of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying potential points of novelty, abstract and drawings), or to any novel one, or any novel combination, of the steps of any method or process so disclosed.

What is claimed is:

1. An anti-acne composition, comprising:
   a fermentation product derived from fermentation of *Leuconostoc* bacterium in an amount of 5% to 20% by weight of the composition;
   water in an amount of 75% to 95% by weight of the composition; and
   at least one of xanthan gum or an oil in water emulsifier in an amount of 2.5% to 10% by weight of the composition;
   wherein the fermentation product comprises an antimicrobial peptide derived from the *Leuconostoc* bacterium.

2. The anti-acne composition according to claim 1, wherein the antimicrobial peptide has a pH ranging from about 3.0 to about 5.0.

3. The anti-acne composition according to claim 1, wherein the fermentation product comprises a mixture of salicylates selected from the group consisting of sodium salicylate, $C_7H_5NaO_3$, methyl salicylate, $C_8H_8NaO_3$, and combinations thereof.

4. The anti-acne composition according to claim 1, wherein the composition inhibits the growth of *Propionibacterium acnes*.

5. The anti-acne composition according to claim 1, comprising the emulsifier.

* * * * *